United States Patent [19]

Nissen et al.

[11] Patent Number: 5,175,113
[45] Date of Patent: Dec. 29, 1992

[54] MODIFIED $\beta_2$-MICROGLOBULIN

[75] Inventors: Mogens H. Nissen, Frederiksberg; Jesper Zeuthen, Virum; Flemming S. Larsen, Vanlose; Lars Thim, Gentofte; Mogens Christensen, Copenhagen, all of Denmark

[73] Assignee: Novo Nordisk A/S, Denmark

[21] Appl. No.: 550,919

[22] Filed: Mar. 29, 1990

Related U.S. Application Data

[62] Division of Ser. No. 3,436, Jan. 15, 1987, Pat. No. 5,051,371.

[30] Foreign Application Priority Data

Jan. 16, 1986 [DK] Denmark .................. 215/86

[51] Int. Cl.$^5$ .................. G01N 33/577; G01N 33/53; C07K 15/28
[52] U.S. Cl. .................. 436/548; 436/518; 436/804; 435/7.1; 435/7.5; 435/7.92; 435/7.93; 424/85.8; 530/387.9; 530/388.85; 530/391.1; 530/391.3; 530/403
[58] Field of Search .................. 436/548, 547, 518, 529, 436/530, 804; 530/300, 324, 325, 326, 830, 834, 387, 388, 388.25, 387.9, 387.3, 388.85, 391.1, 391.3, 403; 930/260; 424/85.8

[56] References Cited

U.S. PATENT DOCUMENTS 4,376,110 3/1983 David et al. .................. 436/513

FOREIGN PATENT DOCUMENTS 2030294A 8/1979 United Kingdom .

OTHER PUBLICATIONS

Hopp et al, "Prediction of protein antigenic determinants from amino acid sequences" Proc. Natl. Acad. Sci. USA, 78(6):3824–3828 (Jun. 1981).
Hopp et al, "A Computer Program for Predicting Protein Antigenic Determinants" Mol. Immunol. 20(4):483–489 (1983).
Taggart et al, "Stable Antibody-Producing Murine Hybridomas", Science 219:1228–30 (Mar. 11, 1983).
Wide "Chapter 13 Noncompetitive Versus Competitive Binding Assays" in Principles of Competitive Protein-Binding Assays, 2nd Ed. pp. 243–254 (1983).

(List continued on next page.)

Primary Examiner—Esther L. Kepplinger
Assistant Examiner—Carol E. Bidwell
Attorney, Agent, or Firm—Sterne, Kessler, Goldstein & Fox

[57] ABSTRACT

Substantially pure modified $\beta_2$-microglobulin (m$\beta_2$m) of the formula I $$R_1-Cys-R_2-X$$
$$Y-R_3-Cys-R_4$$

wherein $R_1$ is 24-amino acid residue, with the sequence Ile-Gln-Arg-Thr-Pro-Lys-Ile-Gln-Val-Tyr-Ser-Arg-His-Pro-Ala-Glu-Asn-Gly-Lys-Ser-Asn-Phe-Leu-Asn, $R_2$ is a 30-amino acid residue with the sequence Tyr-Val-Ser-Gly-Phe-His-Pro-Ser-Asp-Ile-Glu-Val-Asp-Leu-Leu-Lys-Asn-Gly-Glu-Arg-Ile-Gly-Lys-Val-Glu-His-Ser-Asp-Leu-Ser, $R_3$ is a 20-amino acid residue with the sequence Trp-Ser-Phe-Tyr-Leu-Leu-Tyr-Tyr-Glu-Phe-Thr-Pro-Thr-Glu-Lys-Asp-Glu-Tyr-Ala, $R_4$ is a 19-amino acid residue with the sequence Arg-Val-Asn-His-Val-Thr-Leu-Ser-Gln-Pro-Lys-Ile-Val-Lys-Trp-Asp-Arg-Asp-Met, X is Phe, Phe-Ser, or Phe-Ser-Lys, and Y is Asp, Lys-Asp, or Ser-Lys-Asp is disclosed. The presence of the protein in body fluids is a diagnostic and/or prognostic marker for the development of a variety of disorders such as different types of cancer and diseases involving the immune system. Also disclosed are specific anti-m$\beta_2$m antibodies used for the detection and quantification of m$\beta_2$m.

13 Claims, 9 Drawing Sheets

OTHER PUBLICATIONS

ATCC (American Type Culture Collection) Catalogue of Cell Lines and Hybridomas Fifth Edition, pp. 212, 217 and 222 (1985).

The Calbiochem Biochemical and Immunochemical Catalog, pp. 204-205 (1985).

Cunningham, et al., *Biochem.* 12(24):4811-4821 (1973).

Suggs et al., *Proc. Natl. Acad. Sci. USA* 78(11):6613-6617 (1981).

Plesner et al., *Scand. J. Immunol.* 11:341-351 (1980).

Bhalla et al., *Clinical Chemistry* 31(8):1411 (1985).

Peterson et al., *Proc. Nat. Acad. Sci. USA* 71(1):35-39 (1974).

Terhorst et al., *Cell* (23):771-780 (1981).

Nissen, et al. *Clinica Chimica Acta* 141:41-50 (1984).

Plesner et al., *Scand J. Immunol.* 9:247-254 (1979).

Plesner, T. *Allergy* 35:627-637 (1980).

Plesner, et al., *Scand. J. Clin. Lab. Invest.* 35:729-735 (1975).

β₂-MICROGLOBULIN

Ile. .Phe Ser Lys Asp .Met
1. .56 57 58 59. .99
S—S
S—S

A-CHAIN 1                                        10                                        20
ILE GLN ARG THR PRO LYS ILE GLN VAL TYR SER ARG HIS PRO ALA GLU ASN GLY LYS SER ASN PHE LEU ASN CYS

B-CHAIN 1                                        10                                        20
Y TRP SER PHE TYR LEU LEU TYR TYR THR GLU PHE THR PRO THR GLU LYS ASP GLU TYR ALA CYS ARG VAL ASN

MODIFIED β₂-MICROGLOBULIN

FIG. 1A

TYR VAL SER GLY PHE HIS PRO SER ASP ILE GLU VAL ASP LEU LEU LYS ASN GLY GLU ARG PHE GLY LYS VAL GLU HIS SER ASP LEU SER X
          30                              40                              50

HIS VAL THR LEU SER GLN PRO LYS ILE VAL LYS TRP ASP ARG ASP MET Y
          30                              40

X = Phe, Phe-Ser, or
    Phe-Ser-Lys

Y = Asp, Lys-Asp, or
    Ser-Lys-Asp

FIG.1B b = ARBITRARY BACKGROUND LEVEL b = ARBITRARY BACKGROUND LEVEL

MODIFIED $\beta_2$-MICROGLOBULIN

CROSS REFERENCE TO APPLICATION

This is a divisional of co-pending application Ser. No. 07/003,436, filed Jan. 15, 1987 now U.S. Pat. No. 5,051,371 issued Sep. 24, 1991.

This invention relates generally to modified $\beta_2$-microglobulins (m$\beta_2$m) of the formula I below, polyclonal and monoclonal antibodies raised against said m$\beta_2$m serving as a diagnostic and/or prognostic marker for the development of a variety of disorders such as cancer and diseases involving the immune system, to a method for producing said polyclonal and monoclonal antibodies, and to their use as diagnostic and prognostic aids.

The invention further relates to pharmaceutical compositions comprising m$\beta_2$m or/and its precursor $\beta_2$-microglobulin ($\beta_2$m) to be used as biological response modifying agents, and pharmaceutical compositions comprising anti m$\beta_2$m antibodies also to be used as biological response modifying agents.

The modified $\beta_2$-microglobulins according to the invention have the general formula I

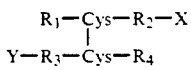

wherein $R_1$ is 24-amino acid residue, with the sequence Ile-Gln-Arg-Thr-Pro-Lys-Ile-Gln-Val-Tyr-Ser-Arg-His-Pro-Ala-Glu-Asn-Gly-Lys-Ser-Asn-Phe-Leu-Asn, $R_2$ is a 30-amino acid residue with the sequence Tyr-Val-Ser-Gly-Phe-His-Pro-Ser-Asp-Ile-Glu-Val-Asp-Leu-Leu-Lys-Asn-Gly-Glu-Arg-Ile-Gly-Lys-Val-Glu-His-Ser-Asp-Leu-Ser, $R_3$ is a 20-amino acid residue with the sequence Trp-Ser-Phe-Tyr-Leu-Leu-Tyr-Tyr-Thr-Glu-Phe-Thr-Pro-Thr-Glu-Lys-Asp-Glu-Tyr-Ala, $R_4$ is a 19-amino acid residue with the sequence Arg-Val-Asn-His-Val-Thr-Leu-Ser-Gln-Pro-Lys-Ile-Val-Lys-Trp-Asp-Arg-Asp-Met, X is Phe, Phe-Ser, or Phe-Ser-Lys, and Y is Asp, Lys-Asp, or Ser-Lys-Asp

BACKGROUND OF THE INVENTION

Modified $\beta_2$m-microglobulin (m$\beta_2$m) is a variant of $\beta_2$-microglobulin ($\beta_2$m), which variant has been detected in connection with a variety of types of cancer and disorders of the immune system.

Its precursor $\beta_2$m is a serum protein with a molecular mass of 11800 Daltons consisting of a single chain polypeptide consisting of 99 amino acid residues with a disulfide bridge between cysteine residues in positions 25 and 80, and with a known amino acid sequence (1). Structurally $\beta_2$m shows a marked homology to the constant domain in IgG, especially the $C_H3$ domain and the $\alpha_3$ domain of the heavy chain HLA-B7. $\beta_2$m is part of the major histocompatibility complex on cell membranes and is present in free form in body fluids such as serum, spinal fluid, saliva, semen, and colostrum (2,3). In healthy individuals the serum concentration of $\beta_2$m is 50-200 nmol/1 (4).

The serum concentration of $\beta_2$m is elevated in a variety of diseases e.g. rheumatoid arthritis (RA), systemic lupus erythomatosus (SLE), malignant lymphoma (ML), and certain types of lung cancer such as small cell lung cancer (SLC) (5-7). High levels of serum $\beta_2$m in ML decrease during response to chemotherapy, while relapse is generally not accompanied by rising serum $\beta_2$m.

Small cell lung cancer (SLC) is nearly always disseminated at the time of diagnosis and therefore the main treatment is combination chemotherapy. With chemotherapy it is possible to induce remission in more than 80% of all patients, but in most of the cases the tumor will later escape control. The earliest possible diagnosis, preferably at a stage where the disease is still localized, may consequently be crucial for improving the rate of survival of patients suffering from SLC.

Acquired immunodeficiency syndrome (AIDS) is the final culmination of a disease that apparently exists in other forms such as AIDS-related complex or lymphadenopathy syndrome, and in less-manifested states, including the carrier state. Blood-donor screening by use of an antibody to the presumed causative virus (HTLV-III/LAV) has begun. Such testing for the virus only detects exposure to it, not the presence of or the prognosis for development of disease. Also, the antibody test for HTLV-III sometimes fails to detect the presence of the virus (1). Thus, another test is needed that will allow a more quantitative assessment of the response of the immune system to HTLV-III exposure.

$\beta_2$m has received much attention as a possible marker that could be used for diagnosis and monitoring of diseases such as those mentioned above.

It has thus been reported that most AIDS patients tested have $\beta_2$m levels above normal. It has further been reported that increased $\beta_2$m levels have been found in a number of cases even two years before clinical diagnosis of AIDS.

Incubation in vitro of serum from patients with RA, SLE, germ cell tumors and ML have been shown to result in the appearance in crossed radioimmunoelectrophoresis (CRIE) of a $\beta_2$m fraction with "$\alpha$-electrophoretic mobility" (5,8,9). In patients with ML an inverse correlation between the amount of this $\alpha$-fraction and response to chemotherapy has been found.

Ravi B. Bhalla et al.: Clinical Chemistry 31 (1985) p. 1411, have reported that they found the $\alpha$-electrophoretic form of $\beta_2$m or modified $\beta_2$m to be present in all their AIDS patients including those with normal $\beta_2$m levels, and beside that also in a patient who was HTLV-III-negative.

The $\alpha$-electrophoretic form or modified $\beta_2$m (m$\beta_2$m) therefore seems very attractive as a marker for a variety of immunological disorders. M$\beta_2$m is obviously not specific for any of the diseases mentioned above, but measurement thereof will nevertheless be a valuable tool for screening of a large number of samples, or for monitoring of the development of those diseases.

BRIEF DESCRIPTION OF THE INVENTION

Consequently, it has been an object of this invention to develop means for the utilization of m$\beta_2$m as a general marker in the diagnosis and evaluation of the prognosis of cancer and, immunological diseases manifesting themselves by abnormal levels of m$\beta_2$m. This object is attained according to the present invention by providing an efficient method for the detection and measurement of m$\beta_2$m in body fluids. The method makes use of specific polyclonal antibodies obtained in antisera against m$\beta_2$m or specific epitopes thereon, fusing such antibody producing cells with myeloma cells to obtain hybridomas, and selecting hybridoma cells producing monoclonal antibodies which bind specifically to m$\beta_2$m. The invention was made following the elucidation of the chemical structure of m$\beta_2$m.

A biological significance of m$\beta_2$m has till now not been described, but during work on this invention it was surprisingly found that m$\beta_2$m is biologically active as a biological response modifying agent augmenting immunological responses that has already been activated, and that $\beta_2$m in this respect acts as a precursor for the active species m$\beta_2$m. Also, it was found that anti m$\beta_2$m antibodies were able to block the activity of m$\beta_2$m, and thereby suppress the biological response.

As a consequence of these findings it is also an object for this invention to provide for pharmaceutical compositions comprising m$\beta_2$m or/and $\beta_2$m to be used as biological response modifying agents, as well as pharmaceutical compositions comprising anti $\beta_2$m antibodies to be used as biological response blocking agents.

In a first aspect the invention relates to novel modified $\beta_2$-microglobulins of the general formula I above.

In its second aspect the invention relates to an antiserum or polyclonal antibody raised against m$\beta_2$m by immunization of an animal, such as a rodent, with a m$\beta_2$m or another antigen which is capable of inducing the production of anti m$\beta_2$m antibodies in the host.

In a further aspect the invention relates to monoclonal anti-m$\beta_2$m antibodies provided by fusing antibody producing cells from animals immunized with m$\beta_2$m or another suitable antigen with myeloma cells in order to obtain hybridomas each producing a specific monoclonal anti-m$\beta_2$m antibody.

In a still further aspect the invention relates to the use of such specific anti-m$\beta_2$m antibodies in methods for the detection and analysis of m$\beta_2$m human serum or other body fluids, in which methods these antibodies may be used either individually or in combination, and diagnostic kits including an anti-m$\beta_2$m antibody.

In a further aspect the invention relates to pharmaceutical compositions comprising m$\beta_2$m or/and $\beta_2$m in combination with physiologically acceptable carriers, and the use of such pharmaceutical compositions as biological response modifying agents, such as immune stimulating or suppressing agents.

In a yet further aspect the invention relates to pharmaceutical compositions comprising specific anti m$\beta_2$m antibodies in combination with physiologically acceptable carriers, and the use of such compositions as biological response blocking agents.

BRIEF DESCRIPTION OF THE DRAWING

The invention will be described in detail below with reference to the drawing, wherein FIG. 1A and 1B show the amino acid sequence of the modified $\beta_2$-microglobulins of the invention compared to the sequence of $\beta_2$m.

FIG. 5 shows the result from titration in ELISA of an antiserum according to the invention.

DETAILED DESCRIPTION OF THE INVENTION

Figure 2:
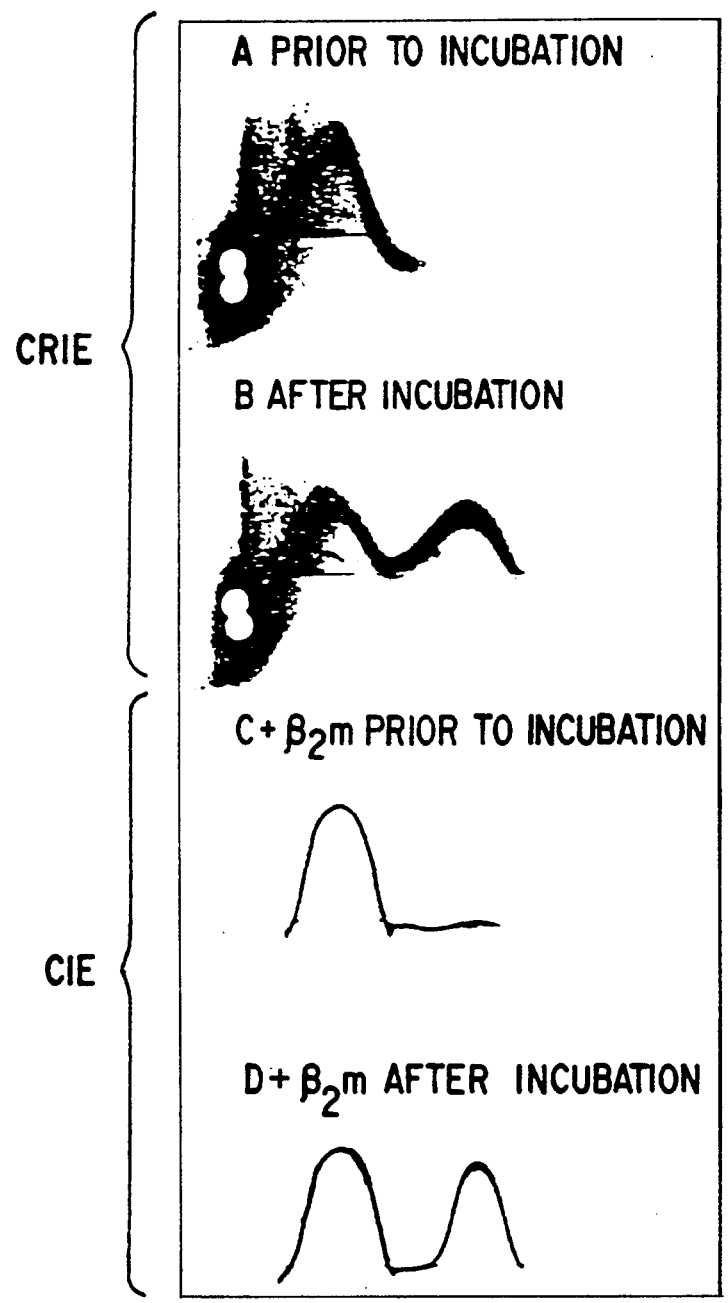
FIG. 2 shows crossed radio immuno electrophoreses (CRIE) and crossed immuno electrophoreses (CIE) analysis of human serum and human serum with added m$\beta_2$m.

Modified $\beta_2$-microglobulin is defined as the fraction of $\beta_2$m that has a relative mobility of 2.0 compared to the native protein when analyzed in CRIE.

The modified $\beta_2$-microglobulin according to the invention was obtained by isolating it together with $\beta_2$m from serum samples from patients with histologically verified small cell anaplastic lung cancer (WHO II), and subsequent separation from $\beta_2$m.

The isolation of m$\beta_2$m and $\beta_2$m from the serum was performed by gel filtration after incubation for five days at 20° C.

Fractions containing m$\beta_2$m and $\beta_2$m was chromatofocused at pH 7-4 in order to separate m$\beta_2$m from $\beta_2$m, and the m$\beta_2$m containing fraction was subsequently purified by gel filtration.

The product of the invention, m$\beta_2$m was characterized physico-chemically and biochemically by CIE, CRIE, sodium dodecylsulfate polyacrylamide electrophoresis (SDS-PAGE), and analytical isoelectric focusing (IEF), and shown to be identical to the $\alpha$ electrophoretic form of $\beta_2$m, or m$\beta_2$m as defined in the literature.

The m$\beta_2$m according to the invention may also be obtained by any other combination of methods known in the art, by which molecules are fractionated according to their size and isoelectric point.

It is further contemplated that $\beta_2$m and m$\beta_2$m for the purposes of the invention may be produced by gene technology or peptide synthesis. Also, m$\beta_2$m may conveniently be produced enzymatically from $\beta_2$m.

The m$\beta_2$m according to the invention revealed an apparent molecular weight of 15,000 in unreduced form, and splits up into two minor peptides of molecular weight below 12,000 in reduced form, when analyzed by SDS-PAGE. In unreduced form m$\beta_2$m had a pI of 5.3 in analytical IEF.

The product was subjected to amino acid sequencing and shown to have the following general formula I

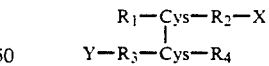

wherein $R_1$ is 24-amino acid residue, with the sequence Ile-Gln-Arg-Thr-Pro-Lys-Ile-Gln-Val-Tyr-Ser-Arg-His-Pro-Ala-Glu-Asn-Gly-Lys-Ser-Asn-Phe-Leu-Asn, $R_2$ is a 30-amino acid residue with the sequence Tyr-Val-Ser-Gly-Phe-His-Pro-Ser-Asp-Ile-Glu-Val-Asp-Leu-Leu-Lys-Asn-Gly-Glu-Arg-Ile-Gly-Lys-Val-Glu-His-Ser-Asp-Leu-Ser, $R_3$ is a 20-amino acid residue with the sequence Trp-Ser-Phe-Tyr-Leu-Leu-Tyr-Tyr-Thr-Glu-Phe-Thr-Pro-Thr-Glu-Lys-Asp-Glu-Tyr-Ala, $R_4$ is a 19-amino acid residue with the sequence Arg-Val-Asn-His-Val-Thr-Leu-Ser-Gln-Pro-Lys-Ile-Val-Lys-Trp-Asp-Arg-Asp-Met, X is Phe, Phe-Ser, or Phe-Ser-Lys, and Y is Asp, Lys-Asp, or Ser-Lys-Asp.

The amino acid sequence for the $R_1$-Cys-$R_2$-X-chain (A-chain) is identical to the published sequence of residues 1-56 (58) in the native $\beta_2$m with the only exception of amino acid residue 42 where the residue according to the invention is Asn, whereas the published sequence indicates Asp. The sequence according to the invention is, however, in accordance with the sequence deduced from cloned cDNA by Suggs et al.: Proc. Natl. Acad. Sci. USA 78 (1981) pp. 6613-6617, who also indicate Asn in position 42.

The sequence of the C-terminal end of the $R_1$-Cys-$R_2$-X-chain was determined both by Edman degradation from the N-terminal end and by carboxypeptidase digestion from the C-terminal end, and it was found that the product predominantly consisted of the peptide wherein X is Phe, and Y is Asp. The C-terminal determination was complicated by the presence of serine residues in positions 52, 55 and 57.

The amino acid sequence of the Y-$R_3$-Cys-$R_4$-X-chain (B-chain) is identical to the residues (57) 59-99 in the published sequence of native $\beta_2$m.

As indicated above m$\beta_2$m has been found in the body fluids of patients suffering from a number of diseases involving the immune system. Consequently m$\beta_2$m is a potent marker for these diseases, and a rapid, easily performed, and reliable method for detecting the presence of m$\beta_2$m, and measuring the amount present, is most desirable.

According to the invention this is obtained by the use of anti-m$\beta_2$m antibodies obtained by immunizing an animal, such as a rodent, with an antigen capable of raising anti-m$\beta_2$m antibodies in said animal.

Based on the elucidation of the chemical structure of m$\beta_2$m provided, it could be suggested that specific antibodies against m$\beta_2$m could be obtained by using as antigens synthetic peptide fragments corresponding to the sequences adjacent to the site of proteolytic cleavage, i.e. peptides corresponding to partial sequences of the segments defined as either -$R_2$-X or Y-$R_3$-of Formula I coupled to a suitable carrier protein such as keyhole limpet hemocyanin (KLH). In the examples shown herein, the partial sequence of the segment -$R_2$-X; Lys-Val-Glu-His-Ser-Asp-Leu-Ser-Phe was coupled via the N-terminal end (Lys) to KLH as the carrier.

The ideal laboratory method for measuring m$\beta_2$m should be specific (e.g. not influenced by the presence of $\beta_2$m), accurate, precise, easily standardized, fast, inexpensive, and facile. The methods such as CRIE presently available do not meet all of these criteria simultaneously. Especially they are very time consuming, and the results obtained are only semiquantitative.

One of the objects of the invention is therefore to provide for a method for measuring m$\beta_2$m in human body fluids, which method overcomes the drawbacks of the methods mentioned above.

This aspect of the invention is based on the surprising observation that by using appropriate immunization, screening, and selection procedures it is possible to isolate cell lines (hybridomas), which produce monoclonal antibodies that will bind specifically to epitopes present on m$\beta_2$m only, and not on e.g. $\beta_2$m.

The antigen used for the immunization may be m$\beta_2$m, but other antigens selected for their ability to raise anti m$\beta_2$m antibodies, which will bind specifically to epitopes on m$\beta_2$m, may also be used. Generally speaking antigens of the general formula II

R-Z        II wherein R is a carrier protein, and Z is a peptide of the formula $R_2'$-X or $R_3'$-Y, wherein X and Y are defined as in formula I, $R_2'$ is a peptide with from 1 to 30 amino acid residues corresponding to a fragment from the C-terminal end of $R_2$ as defined in formula I, and $R_3'$ is a peptide with from 1 to 20 amino acid residues corresponding to a fragment from the N-terminal end of $R_3$ as defined in formula I.

In one instance an antigen comprising the amino acid residues -Lys-Val-Glu-His-Ser-Asp-Leu-Ser-Phe with a free C-terminal end and the N-terminal end coupled to keyhole limpet hemocyanin (KLH) was used successfully to produce antisera as well as monoclonal antibodies binding specifically to epitopes in the nine C-terminal amino acid residues in the A-chain of m$\beta_2$m.

The immunization was performed in mice by subcutaneously injection several times of the antigen and subsequent boosting intravenously with the antigen. After appropriate time the mice were sacrificed, and their spleens removed for fusion with myeloma cells. The fused cells were derived according to R. T. Taggart and I. M. Samloff: Science 219 (1983) pp. 1228-1230 (APRT+ selection) as described hereinafter.

The screening of the selected hybridoma cultures for specific monoclonal antibodies was performed using an ELISA, and a number of clones found that reacted specifically with m$\beta_2$m without cross-reaction with $\beta_2$m.

The antibodies of the invention may be used in methods for detecting the presence of m$\beta_2$m and also for estimating the amounts present quantitatively.

The detection of the presence of the m$\beta_2$m complete antigen or its characteristic epitope can be carried out in sources or samples of body fluids such as serum, blood, saliva, urine, semen, spinal fluid, colostrum, tissue, biopsies, bronchial lavage and the like.

The detection of m$\beta_2$m based on specific antibodies can be performed by immunoassays, such as the competitive or immunometric ("sandwich") types. In a competitive assay, the purified m$\beta_2$m antigen, or molecule comprising its characteristic epitope, is labelled with a detectable label. The sample suspected of containing the m$\beta_2$m antibody or epitope is incubated with m$\beta_2$m antibody and labelled m$\beta_2$m antigen, and after formation of immune complexes, separation and detection, the level of m$\beta_2$m antigen is readily determined.

Another type of competitive assay involves immobilized m$\beta_2$m antigen or epitope and labelled m$\beta_2$m antibody. The presence of m$\beta_2$m antigen in the source or sample prevents binding of antibody to immobilized antigen or epitope, thus providing an inverse measure of the presence of antigen.

In a competitive type assay, the antibody may also be immobilized on a solid phase, either previous to or subsequent to the formation of the immune complex. For example, a second, anti-mouse IgG, antibody immobilized on a solid phase can be added to the mixture, in what is known as a "double antibody" technique.

In an immunometric (sandwich) assay, one m$\beta_2$m antibody is detectably labelled. Another antibody is insolubilized on a solid phase. Incubation of sample with labelled and insolubilized antibody leads to a sandwich, where, after separation of unbound antibody(ies) the amount of label is proportional to the amount of antigen. Immunometric assays can be carried out in forward, reverse or simultaneous modes, depending on the order of addition of the insolubilized and/or labelled antibodies.

For increased sensitivity in the sandwich system, the procedures described can be modified using biotinylated mβ2m antibody reacting with avidin-peroxidase conjugates.

Other steps such as washing, stirring, shaking, filtering, or pre-assay extraction of mβ2m antigen and the like may, of course, be added to the assays, as may be desired or necessary for a particular situation.

The specific concentrations, the temperature and time of incubation, as well as other assay conditions, can be varied depending on such factors as the concentration of the antigen in the sample, the nature of the sample, and the like. Those skilled in the art will be able to determine operative and optimal assay conditions for each determination while employing routine experimentation. For example, the immunoassay may be run at 4°–37° C., preferably at 26° C., and each incubation step may be as long as 72 hours.

Instead of the mβ2m antigen or characteristic epitope, it is possible to use, in assays, anti-idiotypic antibodies or immunologically active fragments thereof produced by raising antibodies against the binding site of monoclonal antibody mβ2m. Also, instead of the specific mβ2m antibody described herein, it is possible to use equivalent antibodies prepared by screening hybridomas with antigen in a routine manner. The hybridomas are prepared by fusion of lymphocytes sensitized to appropriate purified antigen, and appropriate myelomas.

There are many carriers to which the antibody(ies) can be bound, and which can be used in the present invention. Well-known carriers include glass, polystyrene, polypropylene, polyethylene, dextran, nylon, amyloses, natural and modified celluloses, polyacrylamides, agaroses, and magnetite. The nature of the carrier can be either soluble to some extent or insoluble for purposes of the invention. Those skilled in the art will know many other suitable carriers for binding the antibody(ies), or will be able to ascertain such, using routine experimentation.

Depending on the particular embodiment of the assay of the invention, the antigen or one or more of the antibodies may be coupled with a detectable label such as an enzyme, radioactive isotope, fluorescent compound or metal, chemiluminescent compound, or bioluminescent compound. Furthermore, the binding of these labels to the desired molecule can be done using standard techniques common to those of ordinary skill in the art.

One of the ways in which the desired molecule in any given immunoassay can be detectably labelled is by linking it to an enzyme. This enzyme, in turn, when later exposed to its substrate will react with the substrate in such a manner as to produce a chemical moiety which can be detected, by, for example, spectrophotometric (ELISA system) or fluorometric means. Examples of enzymes that can be used as detectable labels are horseradish peroxidase, malate dehydrogenase, staphylococcal nuclease, delta-5-steroid isomerase, yeast alcohol dehydrogenase, alpha-glycerophosphate dehydrogenase, triose phosphate isomerase, alkaline phosphatase, asparaginase, glucose oxidase, beta-galactosidase, ribonuclease, urease, catalase, glucose-6-phosphate dehydrogenase, glucoamylase, and acetylcholine esterase.

The presence of antigen or antibody (and as a consequence its corresponding mβ2m antigen) can also be detected by labelling the desired molecule with a radioactive isotope. The presence of the radioactive isotope would then be determined by such means as the use of a gamma counter or a scintillation counter. Isotopes which are particularly useful are $^3H$, $^{125}I$, $^{131}I$, $^{32}P$, $^{35}S$, $^{14}C$, $^{51}Cr$, $^{36}Cl$, $^{57}Co$, $^{58}Co$, $^{59}Fe$, $^{75}Se$, $^{111}In$, $^{99m}Tc$, $^{67}Ga$, and $^{90}Y$.

It is also possible to detect the presence of the antigen or antibody by labelling the desired molecule with a fluorescent compound. When the fluorescently labelled molecule is exposed to light of the proper wavelength, its presence can then be detected due to fluorescence of the dye. Among the most important fluorescent labelling compounds are fluorescein isothiocyanate, rhodamine, phycoerythrin, phycocyanin, allophycocyanin, o-phthaldehyde, and fluorescamine.

Fluorescence emitting metal atoms such as Eu (europium), and other lanthanides, can also be used. These can be attached to the desired molecule by means of metalchelating groups, such as DTPA or EDTA.

Another way in which the antigen or antibody can be detectably labelled is by coupling it to a chemiluminescent compound. The presence of the chemiluminescent-tagged immunological molecule is then determined by detecting the presence of luminescence that arises during the course of a chemical reaction. Examples of particularly useful chemiluminescent labelling compounds are luminol, isoluminol, aromatic acridinium ester, imidazole, acridinium salt, and oxalate ester.

Likewise, a bioluminescent compound may also be used as a label. Bioluminescence is a special type of chemiluminescence which is found in biological systems and in which a catalytic protein increases the efficiency of the chemiluminescent reaction. The presence of a bioluminescent molecule would be determined by detecting the presence of luminescence. Important bioluminescent compounds for purposes of labelling are luciferin, luciferase, and aequorin.

Another possible assay technique for mβ2m antigen or its corresponding characteristic epitope is by agglutination, where the mβ2m antibody is bound on latex beads, and presence of the mβ2m antigen is measured by bead aggregation.

Alternatively, the presence of mβ2m antibody can be detected by agglutination of beads coated with mβ2m antigen or epitope.

An alternative use for the mβ2m antibody is in immunohistochemical tissue analysis, by using labelled antibody.

In the methods for detecting the mβ2m antigen mentioned above it is possible to use one specific anti-mβ2m antibody. However, it is also possible in order to enhance the selectivity of the method to use combinations of two or more specific anti-mβ2m antibodies, e.g. one antibody specific for an epitope in the C-terminal end of the A-chain in combination with one antibody specific for an epitope in the N-terminal end of the β-chain.

The materials for use in the assay of the invention are ideally suited for the preparation of a kit. Such a kit may comprise a carrier means being compartmentalized to receive in close confinement one or more container means such as vials, tubes, and the like, each of said container means comprising one of the separate elements to be used in any desired method.

For example, one of the said container means useful in immunometric assays may comprise monoclonal anti-mβ2m antibody bound to a carrier. A second container may comprise soluble, detectably labelled monoclonal anti-mβ2m antibody, in lyophilized form or in solution.

A kit useful for a competitive assay would comprise a first container comprising detectably labelled antigen, and a second container comprising anti-m$\beta_2$m antibody, free or carrier-bound.

In addition, the carrier means may also contain a plurality of containers each of which comprises different, predetermined amounts of antigen. These latter containers can then be used to prepare a standard curve into which can be interpolated the results obtained from the sample containing the unknown amount of antigen.

In a surprising aspect of this invention, purified m$\beta_2$m was shown to augment the cytotoxic activity in mixed lymphocyte cultures (MLC) as well as to stimulate the production of the lymphokine interleukin-2 (IL-2). The interaction of m$\beta_2$m with the major histocompatibility complex (MHC), in which $\beta_2$m is a normal component, leads to activation of cells resulting in, e.g., increased cellular receptor expression for general stimulatory activity such as interleukin-1 (IL-1) and an enhanced expression of receptors of IL-2 and increased endogenous production of this lymphokine. This biological activity of the m$\beta_2$m of this invention has pharmaceutical utility with m$\beta_2$m as a biological response modifying agent of the immune system. Without limiting this invention it is believed that the pharmacological effects of m$\beta_2$m are related both to the effect at the membrane level due to interaction with the MHC or are related to the specific stimulatory effect on IL-2 production.

A stimulatory effect on IL-2 production can augment a range of immunological activities such as stimulation, suppression etc. depending on the state of the immune system at administration of m$\beta_2$m. A particularly important aspect of the stimulation of IL-2 production by m$\beta_2$m is the augmentation of lymphokine activated killing (LAK) mediated by natural killer (NK) cells known to stimulate tumor regression.

The invention is illustrated in more detail in the following examples, which are given for illustrative purposes only, and are not to be construed as limiting the scope of the invention as defined in the appended claims.

EXAMPLE 1

Isolation and Purification of m$\beta_2$m a) Materials and methods:

Materials

Sephadex ® G-75 and Polybuffer Exchanger 94 were both obtained from Pharmacia Fine Chemicals, Uppsala, Sweden. Acrylamide, methylene bis acrylamide and ammonium persulfate were obtained from Serva, Heidelberg, West Germany. Ammediol and sodium dodecylsulfate were purchased from Merck, Darmstadt, West Germany.

Starting material

Serum samples from two patients with histologically verified small cell anaplastic lung cancer (WHO 11) (17) were isolated within six hours after drawing the blood samples and kept frozen at −20° C. until used.

Urinary $\beta_2$m

Urine samples collected from ureamic patients were used for isolation of urinary $\beta_2$m. Proteins were precipitated by 90%–100% ammoniumsulphate at 5000 G for one hour. The precipitate was then solubilized in isotonic saline. The purification procedures were then identical as for serum as described below.

$^{125}$I labelling of protein A 5 mg protein A (Pharmacia Fine Chemicals) was reconstituted in isotonic saline to a final concentration of 1.25 g/l. Approximately 12.5 $\mu$l was labelled with 2 mCi $^{125}$I (IM 5681, Amersham, Buckinghamshire, England) by the Bolton-Hunter method. The labelled protein A was then desalted on a PD-10 column (Pharmacia Fine Chemicals), and thereafter diluted in 2 l of phosphate buffered saline (PBS) pH 7.4 containing bovine serum albumin (BSA) (1 g/l), and NaN$_3$ (5 mM) (Merck). It was then used for a period of one month for incubation of immunoelectrophoresis plates.

Crossed immunoelectrophoresis (CIE)

The gel was 1% (w/v) HSA agarose (Litex, Copenhagen, Denmark) in 7.3 mM Tris, 28 mM barbital buffer (pH 8.6) containing 2 mM NaN$_3$. Gel bond film 70 mm×75 mm×0.2 mm (Marine Colloids, Rockland, Me., U.S.A.) was used as support. For first dimension electrophoresis 20 $\mu$l or 40 $\mu$l was applied and electrophoresed at 10 V/cm until a hemoglobin marker had migrated 2.5 cm (approx. 75 minutes). Second dimension electrophoresis against rabbit anti-human $\beta_2$m antibody (Dakopatts, Copenhagen, Denmark) (1 $\mu$l/cm$^2$) was performed at 2 V/cm for at least 16 hours. The plate was then pressed and washed twice in isotonic saline followed by drying and staining with Coomassie Brilliant Blue R-2500 (Sigma, St. Louis, U.S.A.).

Crossed radioimmunoelectrophoresis (CRIE)

For crossed radioimmunoelectrophoresis the same plate as above was incubated overnight with $^{125}$I labelled protein A solution. Non-specifically bound radioactivity was removed by washing the plates in isotonic saline for six hours, and in distilled water overnight. After drying the radioactive precipitate was visualized by autoradiography on Kodak XS-1 film. Time of exposure was normally 2–16 hours (18). CRIE was used to estimate the $\beta_2$m modifying activity since the amount of m$\beta_2$m is considered proportional to the area below the $\beta_2$m precipitate in the alph-electrophoretic region. The area of the two peaks was measured by use of a semiautomatic planimeter as described by Weeke (19). The proportion was expressed on a scale from 0–1 arbitrary unit (A.U.). (The area delineated by the $\beta_2$m precipitate in the $\alpha$ region divided with the total area of both the $\beta_2$m peak and the m$\beta_2$m peak (the $\alpha$ plus $\beta$ fraction). The standard deviation was 0.03 A.U.

Enzyme Linked Immunosorbent Assay of $\beta_2$m

The $\beta_2$m content of various fractions was estimated by a modification of the ELISA method according to 20.

Antisera used: Rabbit anti-human $\beta_2$m antibody (lot 095) and peroxidase-conjugated rabbit anti-human $\beta_2$m antibody (lot 100) were both obtained from DAKO-Immunoglobulins A/S, Copenhagen, Denmark.

Reagents: Reagent A (coating buffer): PBS (0.010M NaH$_2$PO$_4$/NaHPO$_4$; 0.145M NaCl, pH 7.2+0.2). Reagent B (washing and dilution buffer): PBS; 0.1% Tween 20 (v/v) (Merck). 0.5M NaCl. Reagent C (color reagent): 8 mg 1,2-phenylenediamine dihydrochloride (lot 095 (DAKO)), 12 ml 0.1M citric acid phosphate buffer, pH 5.0+0.2, 5 $\mu$l 30% H$_2$O$_2$.

Sera: Standard sera were made by 300 fold dilution of the standards of Pharmacia $\beta_2$m RIA kit Cat. no. 10-6408-01 lot 8577 with reagent B to obtain a working range of 1.33 $\mu$g/l–53.33 $\mu$g/l. Control sera were $\beta_2$m high level and low level both obtained from Pharmacia.

$\beta_2$m ELISA: The wells of the polystyrene microtitre plate (code 239454, Nunc, Copenhagen) were coated with $\beta_2$m antibody by adding 100 $\mu$l $\beta_2$m antibody (2.9 g/l) diluted 1:1000 with reagent A into each well. After 24 hours incubation at room temperature the plate was emptied and washed three times with reagent B. Standard and test samples were diluted with reagent B. 100 μl of the dilution was pipetted into the sensitized wells. Each determination was made in duplicate. The incubation was terminated after 1 hour by emptying the wells followed by washing three times with reagent B. The peroxidase labelled $\beta_2$m antibody (1.3 g/l) was diluted 1:1000 with reagent B and 100 μl of the dilution was pippetted into each well and incubated for 0.5 hour in dark at room temperature. The plate was then emptied and washed three times with reagent B followed by addition of 100 μl colour reagent C into each well and incubated for exactly 15 minutes whereafter the enzyme reaction was stopped by adding 150 μl 1M sulphuric acid into each well. The extinction in the wells of the microtitre plate was estimated by reading on a ELISA reader SLT 210 (Salzburg, Austria) at 492 nm wavelength. All steps in the analysis were performed at room temperature. An 8-channel pipette (Titertek, Teknunc) was used for rapid adding of reagents to the wells.

The standard curve was constructed by plotting the mean value of each duplicate standard determination against concentration on semi-logaritmic paper. The coefficient of variation on duplicates was 9%.

SDS-PAGE

SDS-PAGE was carried out in 2.0 mm thick 13×16.5 cm slab gels. The gel and buffer system were as given by Wycoff (22) and Bury (23) using a linear gradient gel (T=5.2%–15.3%, C=2.6% (bis)). The stacking gel was T=4.2%, C=2.61% (bis). The samples analyzed were heated for 5 minutes at 95° C. in 1% SDS. For alkylation of free thiol groups in unreduced samples iodoacetamide (Sigma) was added to a final concentration of 110 mM. In case of disulfide bonds reduction, dithiothreitol (Sigma) was added to a final concentration of 55 mM. Immediately after heating addition of iodoactamide to a final concentration of 220 mM in unreduced and 110 mM in reduced state was performed.

The following MW standards from Pharmacia Fine Chemicals were used: Phosphorylase b(94,000), albumin (67,000), ovalbumin (43,000), carbonic anhydrase (30,000), trypsin inhibitor (20.100) and α-lactalalbumin (14,400). Bromophenolblue (Riedel de Hauen, Seelze, West Germany) was used as front marker. The gels were stained with Coomassie brilliant blue R-250 according to Fairbanks et al. (24).

Analytical IEF

Analytical IEF was performed on Ampholine ® PAG plates (LKB, Bromma, Sweden) at 25 w/h. After IEF the gel was fixed in 0.14M sulfosalicylic acid and 0.7M trichloroacetic acid in distilled water. The gel was then stained in Coomassie Brilliant Blue R-250 solubilized in destaining solution for 10 minutes at 60° C. Destaining for removal of excess dye substance was performed in 500 ml 25% v/v ethanol mixed with 160 ml 8% v/v acetic acid. For determination of pI the following markers were included: Trypsinogen (pI 9.30), lentil lectin-basic band (pI 8.65), lentil lectin-middle (pI 8.45), lentil lectin-acid (pI 8.15), myoglobin-basic band (pI 7.35), myoglobin-acidic band (pI 6.85), human carbonic anhydrase B (pI 6.55), bovine carbonic anhydrase B (pI 5.85), beta-lactoglobulin A (pI 5.20), soybean trypsin inhibitor (pI 4.55), amyloglucosidase (pI 3.50). Broad calibration kit pI 3.5–10 (Pharmacia Fine Chemicals).

Sequence analysis

Edman degradations were performed with a gas-phase sequencer (Applied Biosystems model 470A) as described in (25). The phenylisothiocyanate amino acids were identified and quantified by reverse-phase HPLC on an IBM cyano column.

In S-aminoethylated peptide the cystein residues were labelled with $^{14}$C during the amino ethylation and cystein residues in these peptides were determined by radioactive counting from 20% of each phenylthiohydantoine amino acid (PTH-a.a.) residue.

Amino acid analysis

Approximately 5 nmol of protein was hydrolyzed in 100 μl of 6N HCl at 110° C. for 24 hours. The amino acid analysis was carried out on a Beckmann model 121 amino acid analyzer. No correction was made for destruction of Trp, Ser, Thr, and Cys.

C-Terminal determination

Approximately 20 nmol of S-aminoethylated A-chain were dissolved in 650 μl of 50 mM pyridine-acetate buffer (pH 6.15). Twenty μl of a norleucine standard (6.5 nmol/μl of water), and 30 μl of a carboxypeptidase Y (Boehringer, Mannheim, West Germany) solution in water (1.7 μg/μl) were added. The incubation was carried out at 37° C. and 100 μl of the digest mixture were removed at times 0, 10, 30, and 120 minutes. The reaction was stopped by addition of 15 μl of acetic acid. After 120 minutes of digestion 5 μl of carboxypeptidase B (Boehringer, Mannheim, West Germany) solution in water (0.02 μg/μl) was added, and samples of 100 μl were removed at times 125 minutes, 180 minutes, and 22 hours, and the enzyme reaction stopped by addition of 15 μl of acetic acid. The samples were lyophilized and submitted to amino acid analysis. Corrections were made for sample volume (internal standard) and for content of free amino acid in buffer (sample at 0 minutes).

Reduction, Alkylation, and S-aminoethylation

Hundred nmol m$\beta_2$m was reduced overnight at room temperature with 5 mM dithiothreitol in a 0.5M Tris-HCl buffer pH 8.1 containing 6M guanidine hydrochloride (Sigma) and 0.005M ethylenediaminotetraacetic acid (EDTA) (Merck). After reduction 50 μCi Iodo(2-$^{14}$C)acetic acid (Amersham, CFA 269, specific activity of 56 mCi/mmol) was added and alkylation was allowed to proceed for 30 minutes in dark, whereafter cold iodoacetic acid was added to 10 mmol and alkylation was allowed to proceed in dark until the A and B chains were separated on HPLC on the same day.

The reaction mixture was fractionated by preparative HPLC on a Waters Nova-pak ® 5μ, C-18 column (4.6 mm×150 mm). The A-buffer was 0.1% (v/v) trifluoroacetic acid in H$_2$O and the B-buffer was 0.07% (v/v) trifluoroacetic acid in acetonitrile. The column was equilibrated with 95% A/5% B, and 200 μl sample was injected. After injection of the sample the column was eluted at a flow rate of 1 ml/minute with 95% A/5% B for 2 minutes, and then with a linear gradient of 1% B-buffer/minute. The absorbance at 280 nm was recorded and fractions were collected. The peptide material was isolated by vacuum centrifugation (Savant vacuum centrifuge) and submitted to sequence analysis.

b) Procedure

Incubation

Approximately 50 ml serum was isolated from two patients suffering from small cell lung cancer, and 3.62 mg purified urinary $\beta_2$m was added. The serum was then incubated for 6 days at 20° C.

In order to monitor and identify m$\beta_2$m during the purification procedures CIE was applied to samples drawn from different fractions during the procedure.

For the purpose of comparison FIG. 2 shows CRIE (FIG. 2a and b) and CIE (FIG. 2c and d) analyses of serum and serum with added m$\beta_2$m, respectively, prior to incubation, and after 3 days of incubation at 20° C.

From FIG. 2 it is clearly shown that the appearance of m$\beta_2$m is a result of the incubation, and it is also clear that the addition of native $\beta_2$m greatly enhances the yield of m$\beta_2$m.

G-75 Sephadex ® gel filtration

Figure 3A:
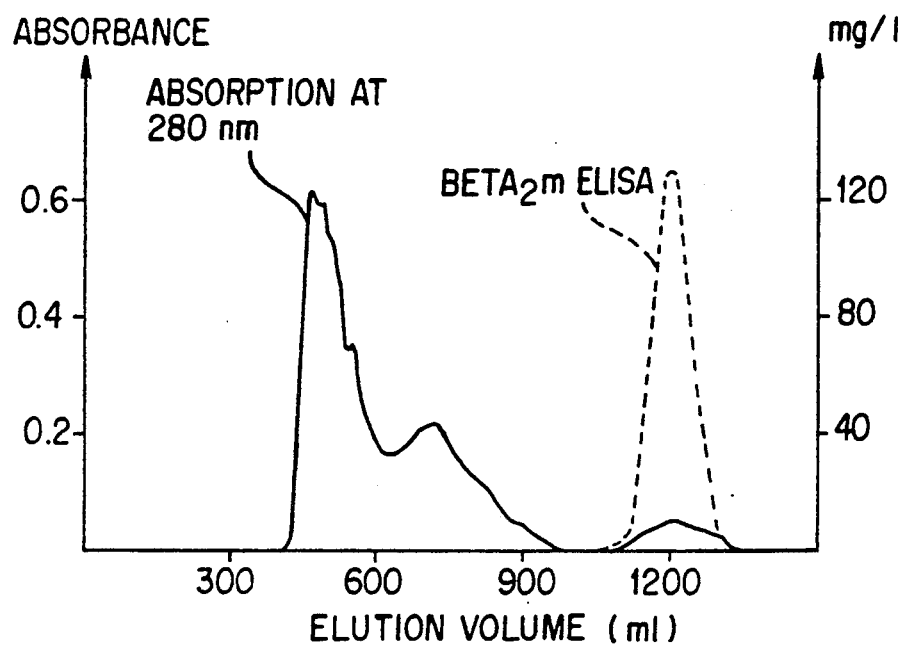
FIG. 3A and 3B show the results of a $\beta_2$m enzyme linked immunosorbent assay (ELISA) of fractions from the chromatographic elution of $\beta_2$m and m$\beta_2$m.

After incubation the serum sample (50 ml) was applied to a column (100×5 cm) packed with Sephadex ® G-75 and equilibrated with 0.025M imidazole/HCl buffer pH 7.4. Elution was carried out with the same buffer at a flow rate of 40 ml/hour. Fractions of 10 ml were collected and analyzed in the $\beta_2$m ELISA. The result of which is shown in FIG. 3A.

Chromatofocusing

Figure 3B:
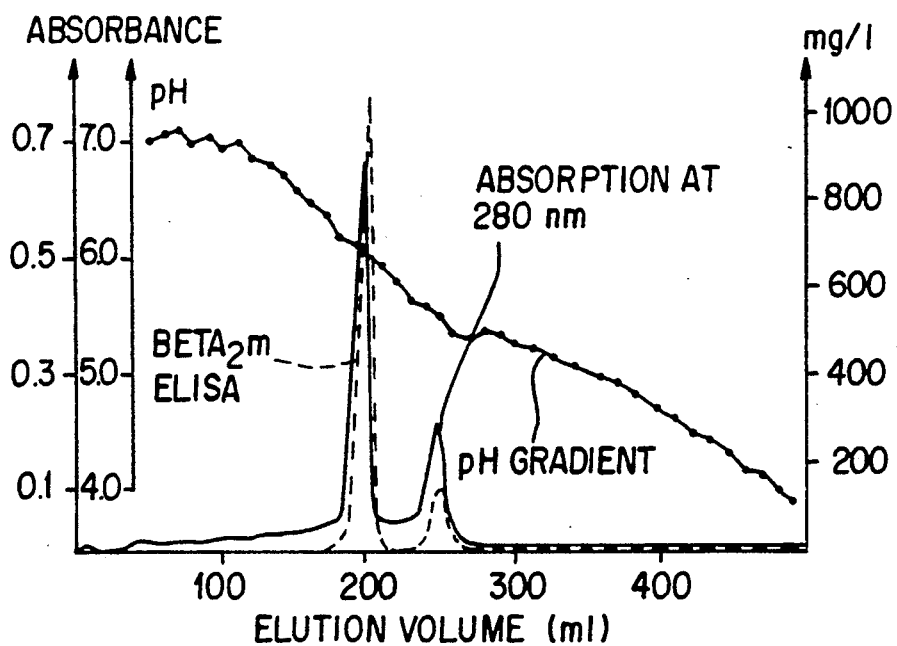
Figure 4:
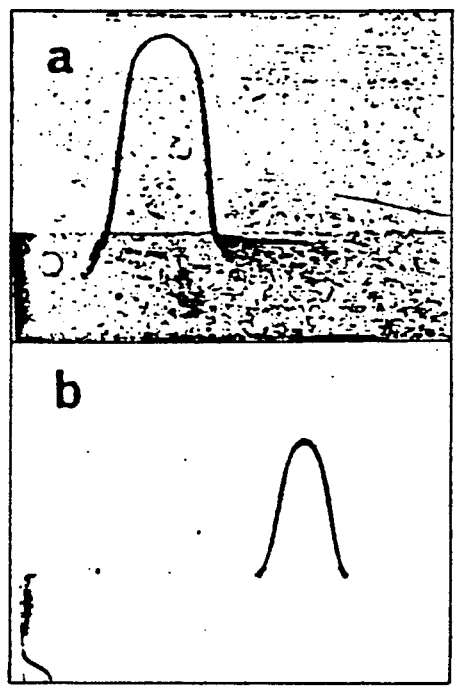
FIG. 4 shows CIE analysis of fractions from the two peaks in FIG. 3B.

Fractions containing $\beta_2$m from the G-75 column was pooled and applied to a column (0.9×70 cm) packed with Polybuffer Exchanger 94 (Pharmacia Fine Chemicals) and equilibrated with imidazol/HCl buffer pH 7.4. $\beta_2$m was eluted with polybuffer 74 diluted 1:8 in distilled water and adjusted to pH 4.0 with HCl. The pH gradient was monitored by measurements of pH in each fraction after elution. Fractions of 5 ml were collected and analyzed in a $\beta_2$m ELISA, the result of which is shown in FIG. 3B. Fractions corresponding to each of the peaks shown in FIG. 3B were pooled and analyzed in CIE, the result of which is shown in FIG. 4. Native $\beta_2$m was eluted at pI 5.7 and m$\beta_2$m at pI 5.3. Purified m$\beta_2$m was obtained by pooling the fractions corresponding to the second peak in FIG. 3B.

Removal of contaminants and final purification

In order to remove contaminants and ammonium sulfate from the product the pooled m$\beta_2$m-containing fractions were precipitated with 90–100% ammonium sulfate at 5000 G for one hour, whereafter the precipitate was solubilized in isotonic saline and applied to a column packed with Sephadex ® G-25 and equilibrated with 1M acetic acid. Elution was performed with the same buffer, and m$\beta_2$m-containing fractions were pooled.

The product thus obtained was analyzed in CIE and found to be pure m$\beta_2$m as defined above.

Amino acid sequence

The amino acid sequence of the m$\beta_2$m according to the invention was determined by the methods indicated above.

The result of the N-terminal sequence analysis is reproduced in Table 1 below.

TABLE 1

| | N-Terminal amino acid sequence of $\beta_2$m | | | |
|---|---|---|---|---|
| Cyclus No. | PTH-a.a. | Yield (pmol) | PTH-a.a. | Yield (pmol) |
| 1 | Ile | 2022 | Asp | 654 |
| 2 | Gln | 1494 | Trp | 883 |
| 3 | Aeg | 500 | Ser | 190 |
| 4 | Thr | 474 | Phe | 1845 |
| 5 | Pro | 1173 | Tyr | 1293 |
| 6 | Lys | 1091 | Leu | 1572 |
| 7 | Ile | 1383 | Leu | 1905 |
| 8 | Gln | 1361 | Tyr | 1213 |
| 9 | Val | 1415 | Tyr | 1305 |
| 10 | Tyr | 1472 | Thr | 436 |
| 11 | Ser | 73 | Glu | 596 |
| 12 | Arg | 223 | Phe | 1070 |
| 13 | His | 206 | Thr | 196 |
| 14 | Pro* | (636) | Pro* | (636) |
| 15 | Ala | 935 | Thr | 221 |
| 16 | Glu** | (387) | Glu** | (387) |

TABLE 1-continued

| | N-Terminal amino acid sequence of $\beta_2$m | | | |
|---|---|---|---|---|
| Cyclus No. | PTH-a.a. | Yield (pmol) | PTH-a.a. | Yield (pmol) |
| 17 | Asn | 691 | Lys | 456 |
| 18 | Gly | 503 | Asp | 307 |
| 19 | Lys | 536 | Glu | 365 |
| 20 | Ser | 61 | Tyr | 487 |
| 21 | Asn | 559 | Ala | 552 |
| 22 | Phe | 506 | (Cys) | — |
| 23 | Leu | 578 | Arg | 185 |
| 24 | Asn | 318 | Val | 453 |
| 25 | (Cys) | — | Asn | 382 |
| 26 | Tyr | 379 | His | 74 |
| 27 | Val*** | (351) | Val*** | (351) |

Average repetitive yield: 92.2%
*Pro is present in both chains in cyclus No. 14
**Glu is present in both chains in cyclus No. 16
***Val is present in both chains in cyclus No. 27

As indicated by these results two PTH-a.a. residues are liberated in approximately equimolar amount in each degradation cycle, showing that the molecule consists of two chains.

Amino acid composition

The amino acid composition was determined as indicated above, and the result is tabulated for both m$\beta_2$m and $\beta_2$m below.

TABLE 2

| Amino acid composition of modified and native $\beta_2$-microglobulin | | |
|---|---|---|
| | Amino acid residue per molecule | |
| Amino acid | m$\beta_2$m | Native $\beta_2$-M |
| Asx* | 11.3 | 12 |
| Thr | 5.6 | 5 |
| Ser | 8.5 | 9 |
| Glx* | 11.8 | 11 |
| Pro | 6.4 | 5 |
| Gly | 5.4 | 3 |
| Ala | 3.9 | 2 |
| Cys ½ | 1.7 | 2 |
| Val* | 7.0 | 7 |
| Met* | 1.1 | 1 |
| Ile | 4.3 | 5 |
| Leu* | 7.6 | 7 |
| Tyr | 5.3 | 6 |
| Phe | 4.6 | 5 |
| Lys* | 7.0 | 8 |
| His | 3.7 | 4 |
| Arg* | 5.3 | 5 |
| Trp | n.d. | 2 | n.d. = not determined
*amino acid used for normalization

Due to impurities in the protein preparation, it is not possible to deduce the exact amino acid composition of the m$\beta_2$m from the analysis, but from Table 2 it is seen that the amino acid composition of m$\beta_2$m is close to that of native $\beta_2$m.

$R_1$-Cys-$R_2$-X-chain (A-chain)

The $R_1$-Cys-$R_2$-X-chain of the m$\beta_2$m was isolated by reverse phase HPLC of the reduced and S-aminoethylated protein. By sequencing of this peptide amino acid residues nos. 1–56 could be determined. The result of the sequencing is tabulated below:

TABLE 3

| AMINO ACID SEQUENCE OF THE S-AMINOETHYLATED A-CHAIN OF THE m$\beta_2$m | | | | |
|---|---|---|---|---|
| Cyclus No. | PTH-A.A. | Yield (pmol) | Cyclus No. | PTH-A.A. | Yield (pmol) |
| 1 | Ile | 7789 | 31 | His | 422 |
| 2 | Gln | 2656 | 32 | Pro | 671 |
| 3 | Arg | 1024 | 33 | Ser | 106 |
| 4 | Thr | 1895 | 34 | Asp | 457 |

TABLE 3-continued

AMINO ACID SEQUENCE OF THE
S-AMINOETHYLATED A-CHAIN OF THE m$\beta_2$m

| Cyclus No. | PTH-A.A. | Yield (pmol) | Cyclus No. | PTH-A.A. | Yield (pmol) |
|---|---|---|---|---|---|
| 5 | Pro | 3500 | 35 | Ile | 566 |
| 6 | Lys | 7625 | 36 | Glu | 373 |
| 7 | Ile | 4655 | 37 | Val | 767 |
| 8 | Gln | 3470 | 38 | Asp | 276 |
| 9 | Val | 4950 | 39 | Leu | 721 |
| 10 | Tyr | 4006 | 40 | Leu | 810 |
| 11 | Ser | 495 | 41 | Lys | 352 |
| 12 | Arg | 1119 | 42 | Asn | 345 |
| 13 | His | 978 | 43 | Gly | 239 |
| 14 | Pro | 2295 | 44 | Glu | 136 |
| 15 | Ala | 3650 | 45 | Arg | 187 |
| 16 | Glu | 1675 | 46 | Ile | 328 |
| 17 | Asn | 1475 | 47 | Glu | 154 |
| 18 | Gly | 1749 | 48 | Lys | 203 |
| 19 | Lys | 5410 | 49 | Val | 213 |
| 20 | Ser | 166 | 50 | Glu | 148 |
| 21 | Asn | 1542 | 51 | His | 58 |
| 22 | Phe | 2214 | 52 | Ser | 17 |
| 23 | Leu | 2239 | 53 | Asp | 92 |
| 24 | Asn | 1200 | 54 | Leu | 166 |
| 25 | — | — | 55 | Ser | 8 |
| 26 | Tyr | 1427 | 56 | Phe | 193 |
| 27 | Val | 1660 | 57 | — | — |
| 28 | Ser | 173 | 58 | — | — |
| 29 | Gly | 783 | 59 | — | — |
| 30 | Phe | 1359 | | | |

Average repetitive yield: 96.9% (a.a. 1-20), 90.9% (a.a. 20-56)

The position of the cystein residue in position 25 was based on radioactive counting of an aliquot of each PTH-a.a. residue.

On this chain C-terminal determination of the amino acid sequence was performed by carboxypeptidase digestion of the S-aminoethylated chain. The result of this analysis is shown in the following Table 4.

TABLE 4

C-TERMINAL DETERMINATION OF THE
S-AMINOETHYLATED A-CHAIN OF m$\beta_2$m
WITH CARBOXYPEPTIDASE Y AND B

| A.a. | 10 min. | 30 min. | 120 min. | 125 min. | 180 min. | 22 h |
|---|---|---|---|---|---|---|
| Asp. | 0.7 | 1.1 | 1.5 | 1.6 | 1.7 | 3.5 |
| Thr | 0 | 0 | 0 | 0 | 0 | 1.8 |
| Ser | 2.3 | 2.7 | 3.2 | 3.2 | 3.6 | 6.9 |
| Glu | 0.5 | 1.0 | 1.5 | 1.6 | 2.1 | 5.6 |
| Pro | 0 | 0 | 0 | 0 | 0.9 | 1.9 |
| Gly | 0.1 | 0.3 | 0.4 | 0.4 | 0.6 | 2.4 |
| Ala | 0 | 0 | 0 | 0 | 0.2 | 1.1 |
| Val | 0 | 0.5 | 0.8 | 0.9 | 1.2 | 4.1 |
| Ile | 0.2 | 0.4 | 0.6 | 0.6 | 0.8 | 3.9 |
| Leu | 2.7 | 3.5 | 3.6 | 3.6 | 3.6 | 4.9 |
| Tyr | 0 | 0.1 | 0.3 | 0.3 | 0.4 | 1.9 |
| Phe | 1.5 | 2.5 | 2.6 | 2.5 | 2.7 | 3.2 |
| Lys | 0.3 | 0.3 | 0.6 | 0.7 | 1.0 | 2.8 |
| Hios | 0.3 | 0.5 | 0.7 | 0.8 | 1.3 | 2.6 |
| Arg | 0 | 0.2 | 0.3 | 0.3 | 0.5 | 2.0 |

From this table it may be deduced that in the product X in formula I predominantly is Phe, to a lesser extent Phe-Ser, and only minute amounts, where X is Phe-Ser-Lys.

Y-R$_3$-Cys-R$_4$-chain (B-chain)

The result of the sequence analysis of the S-aminoethylated Y-R$_3$-Cys-R$_4$-chain is shown in table 5 below:

TABLE 5

AMINO ACID SEQUENCE OF THE
S-AMINOETHYLATED B-CHAIN OF THE m$\beta_2$m

| Cyclus No. | PTH-A.A. | Yield (pmol) |
|---|---|---|
| 1 | Asp | 2979 |
| 2 | Trp | 3770 |
| 3 | Ser | 406 |
| 4 | Phe | 3941 |
| 5 | Tyr | 3634 |
| 6 | Leu | 3562 |
| 7 | Leu | 3946 |
| 8 | Tyr | 3036 |
| 9 | Tyr | 3315 |
| 10 | Thr | 512 |
| 11 | Glu | 2128 |
| 12 | Phe | 2581 |
| 13 | Thr | 448 |
| 14 | Pro | 1353 |
| 15 | Thr | 292 |
| 16 | Glu | 1068 |
| 17 | Lys | 1302 |
| 18 | Asp | 690 |
| 19 | Glu | 669 |
| 20 | Tyr | 1170 |
| 21 | Ala | 1005 |
| 22 | — | — |
| 23 | Arg | 350 |
| 24 | Val | 1022 |
| 25 | Asn | 586 |
| 26 | His | 304 |
| 27 | Val | 724 |
| 28 | Thr | 94 |
| 29 | Leu | 400 |
| 30 | Ser | 37 |
| 31 | Gln | 207 |
| 32 | Pro | 261 |
| 33 | Lys | 307 |
| 34 | Ile | 244 |
| 35 | Val | 281 |
| 36 | Lys | 280 |
| 37 | Trp | 153 |
| 38 | Asp | 112 |
| 39 | Arg | 141 |
| 40 | Asp | 167 |
| 41 | Met | 35 |

Average repetitive yield: 87.4%.

As above the position of the cysteine residue in position 22 is based on radioactive counting of an aliquot of each PTH-a.a. residue. The sequence above is identical to the sequence of residues 59–99 in the published sequence of $\beta_2$m.

EXAMPLE 2

Preparation of polyclonal antisera

RBF/Dn-strain mice (obtained from the Jackson Laboratory, Bar Harbor, Me., USA) were immunized three times at biweekly intervals with the synthetic peptide Lys-Val-Glu-His-Ser-Asp-Leu-Ser-Phe coupled via the N-terminus to keyhole limpet hemocyanin (KLH). The peptide conjugate (25 μg per mouse in PBS, 100 μl) was emulsified 1:1 in Freund's complete adjuvant for the first immunization and in Freund's incomplete adjuvant for the following immunizations, and a total of 200 μl administered subcutaneously (s.c.). Blood samples from immunized mice were obtained from the retroorbital plexus or the eye, and serum samples obtained after centrifugation of the samples after clotting. The specificity of serum samples was evaluated by ELISA using immunoplates (NUNC, Roskilde, Denmark) coated with 1 μg/ml of either native $\beta_2$m or m$\beta_2$m. The serum samples were diluted in tenfold dilutions ($10^{-1}$, $10^{-2}$, $10^{-3}$ and $10^{-4}$) and incubated with the coated plates, and the antibody activity against the respective antigen measured colorimetrically using a rabbit anti-mouse immunoglobulin conjugated with horse radish peroxidase (Dakopatts, Denmark) and the o-phenylenediamine (OPD) substrate reaction.

FIG. 5 illustrates the titration of a representative mouse serum analysed for binding of $m\beta_2m$ (hatched bars) and native $\beta_2m$ (solid bars). The antiserum reacts in a selective fashion with $m\beta_2m$ and appears to be specific for $m\beta_2m$ at dilutions $10^{-4}$ under these conditions. A completely specific polyclonal antiserum against $m\beta_2m$ could be obtained by further absorption with native $\beta_2m$.

EXAMPLE 3

Immunization and Fusion Experiments 1 mg of the peptide Lys-Val-Glu-His-Ser-Asp-Leu-Ser-Phe was mixed with 3 mg KLH (Keyhole Limpet Hemocyanin, Calbiochem) and glutaraldehyde (Merck) was added to a final concentration of 0.25% v/v in a total of 1 ml. pH was adjusted to 8.0. The reaction was carried out for 1 hour at room temperature followed by 18 hours at 4° C. Thereafter the mixture was dialyzed against PBS to obtain the conjugate that was used as antigen in the following immunization.

Production of monoclonal antibodies

RBF/Dn-strain mice containing the RB (8.12)5Bnr Robertsonian translocation chromosome (available from the Jackson Laboratory, Bar Harbor, Me., USA) were immunized three times at two-week intervals with the peptide Lys-Val-Glu-His-Ser-Asp-Leu-Ser-Phe coupled via the N-terminal end to KLH. The conjugate (25 μg per mouse in PBS, 100 μl) was emulsified 1:1 in Freund's complete adjuvant for the first injection and incomplete Freund's adjuvant for the following injections and 200 μl administered subcutaneously (s.c.). The mice were boosted intravenously (i.v.) with 10 μg og conjugate in 100 μl PBS 30 days following the last s.c. immunization. After another three days the mice were sacrificed and their spleens removed for fusion with myeloma cells.

Spleen cells from one RBF/Dn mouse ($13.3 \times 10^7$ cells) were fused with $3.5 \times 10^7$ cells of the FOX-NY myeloma line deficient in the selectable enzyme marker loci adenosine phosphoribosyl transferase (APRT$^-$) and hypoxanthine phosphoribosyl transferase (HPRT$^-$) (available from HyClone Laboratories, Logan, Utah, USA). Thus, the exposure of cell fusion mixtures to a medium requiring APRT-activity (APRT$^+$ selection) eliminates both unfused APRT$^-$ myelomas and APRT$^-$ hybridomas (R. T. Taggart and I. M. Samloff: Science 219 (1983) pp. 1228-1230). The fused cells were seeded on Balb/c-strain mouse macrophage feeder layers in a total of ten 96-well microtiter plates (NUNC, Roskilde, Denmark) in a medium consisting of RPMI-1640 with 15% w/v fetal calf serum (Gibco) supplemented with adenine ($7.5 \times 10^{-5}$M), aminopterin ($8 \times 10^{-7}$M) and thymidine ($1.6 \times 10^{-5}$M), (AAT).

Cultures were incubated for 7 days at 37° C. in air containing 5% $CO_2$ before medium was replaced with fresh medium, and after a 4 day incubation period the cultures were subjected to primary screening by an ELISA.

Screening procedure (ELISA)

Microtiterplates (NUNC Immunoplates, NUNC, Roskilde, Denmark) were coated with antigen. The ELISA used was a modification of the procedure described by A. Voller and E. de Savigny (in R. A. Thompson: Techniques in Clinical Immunology, 2nd Ed. (1981) pp. 157-169. Blackwell Scientific Publications, Boston, Mass.). The coating was performed overnight with the antigen in phosphate buffered saline (PBS), 50 μl per well. The plates were emptied and blocked with PBS containing 2% w/v of bovine serum albumin (BSA), 200 μl per well at 20° C. for 1 hour, followed by three washes with PBS-Tween-20 (0.05% v/v Tween-20 in PBS). The undiluted supernatant from a hybridoma culture (50 μl per well) was applied at 20° C. for 1 hour, followed by washing of the plates as described above. The antibody activity against the antigen used for coating was measured colorimetrically by incubating at 20° C. for 1 hour with 100 μg per well of rabbit anti-mouse immunoglobulin conjugated with horse radish peroxidase (Dakopatts, Denmark) diluted 1:1000 in PBS containing 0.5% w/v BSA and, after a further 3 washes, in 0.1M citrate-phosphate buffer of pH 5.0 (citric acid monohydrate: 7.3 g, $Na_2HPO_4.12-H_2O$: 23.87 g diluted to 1 liter), and then incubated as described above with o-phenylenediamine (OPD) substrate (o-phenylenediamine, 2HCl: 8 mg; citrate buffer: 15 ml; $H_2O_2$ (30% v/v): 5 μl). The reaction was stopped after 3 minutes by the addition of 150 μl of 1M $H_2SO_4$ and the absorbance at 492 nm was read with a double beam KONTRON SLT-210 photometer (SLT, Zurich, Switzerland) with the 620 nm reading as reference.

Primary screening

Using 10 microtiterplates coated with the nonapeptide used for immunization, however not coupled with KLH (1 μg/ml), in the above mentioned method, 960 hybridoma culture supernatants were tested. 27 cultures reacted significantly positive and were subjected to further testing.

Figure 6:
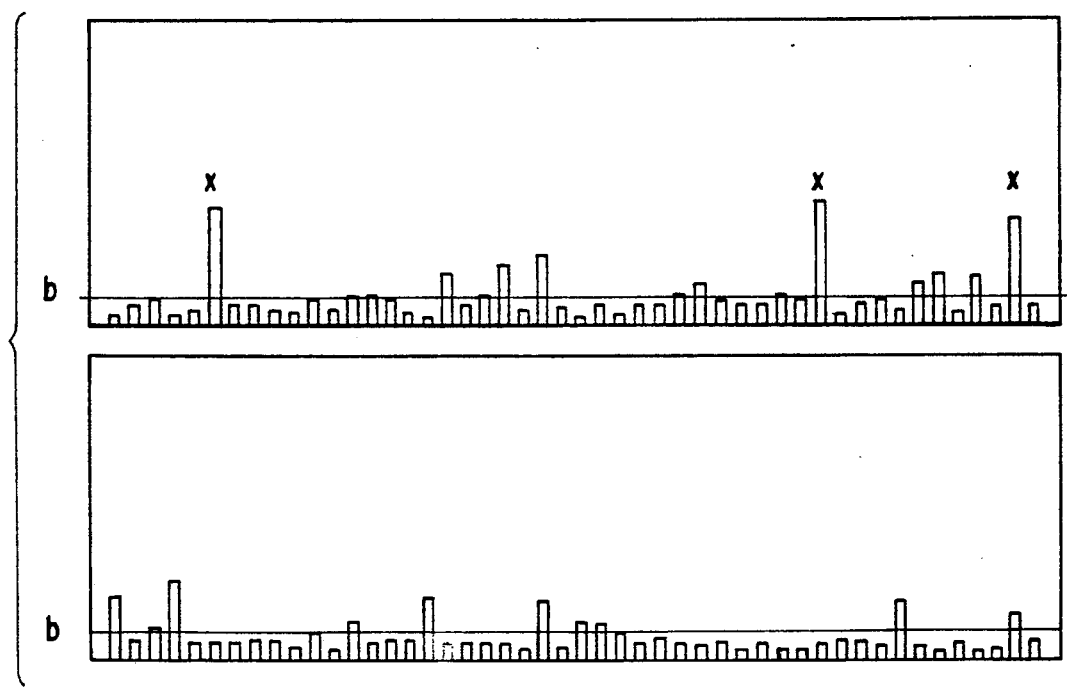
FIG. 6 shows results from the primary screening of anti-m$\beta_2$m antibody producing cultures.
Figure 6:
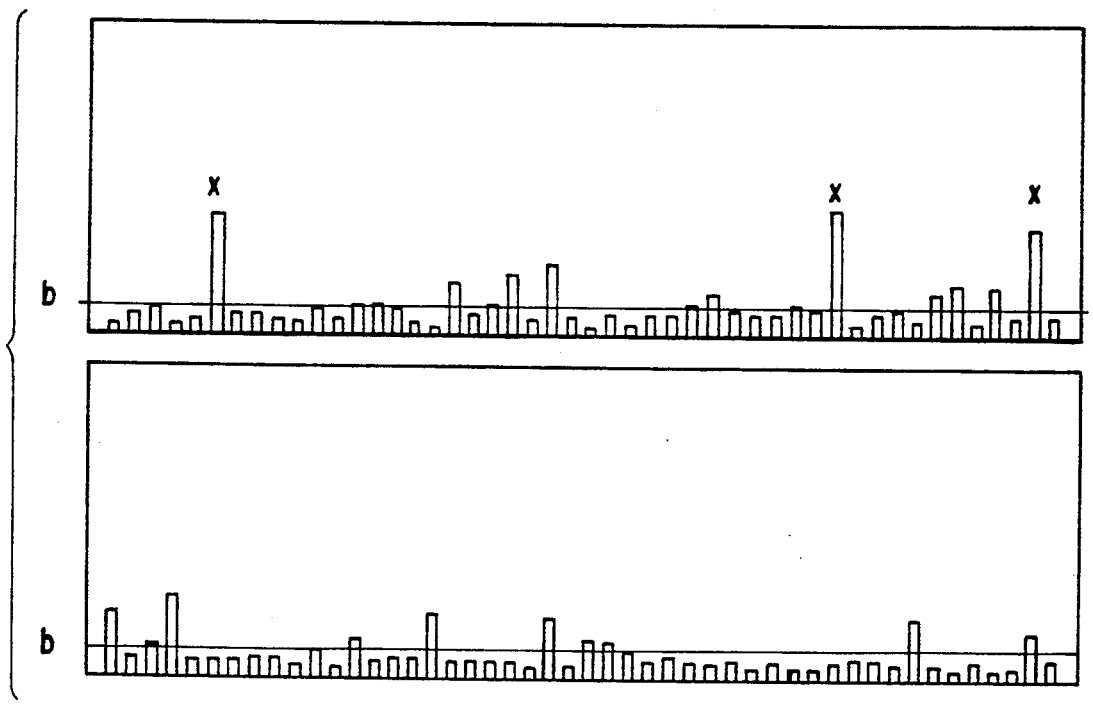

FIG. 6 exemplify the results of the ELISA in the primary screening. The results from one of the ten microtiter plates are shown. The horizontal line represents an arbitrary background level chosen for the primary screening. Only the cultures marked with an x were selected for further testing.

Secondary screening

Microtiter plates were coated with either the nonapeptide, $\beta_2m$ (native) or $m\beta_2m$ (variant) in concentrations of 1 μg/ml, 10 μg/ml and 10 μg/ml respectively. The 27 culture supernatants were applied and the test carried out according to the "screening procedure" above.

Figure 7A:
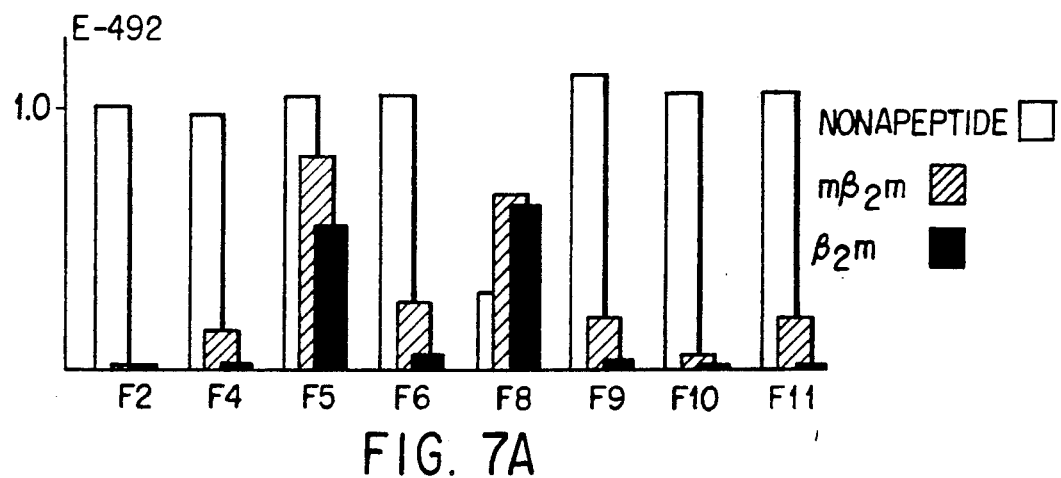
FIG. 7A-7C show the results from the secondary screening in ELISA of cultures selected from the primary screening in FIG. 6.
Figure 7B:
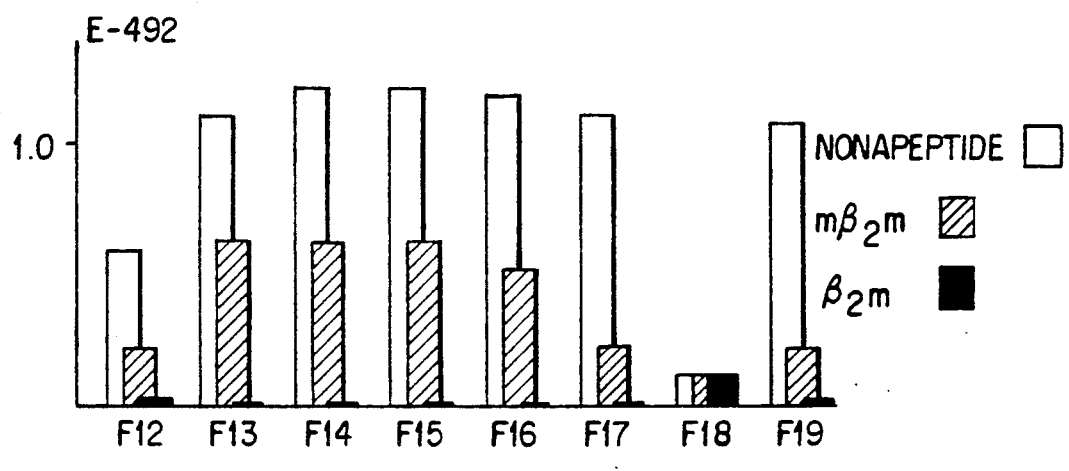
Figure 7C:
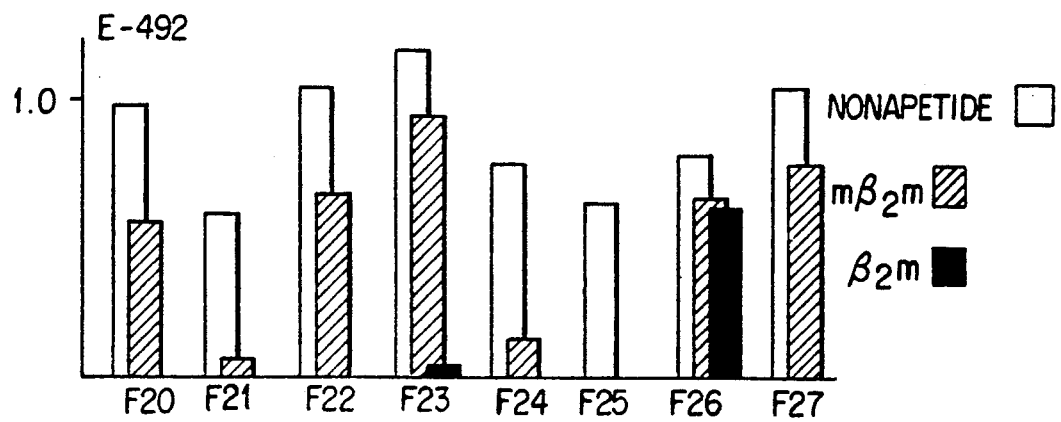

In FIG. 7 the results of the secondary screening is shown for the selected cultures from the primary screening, except cultures F1, F3, and F7 that were negative in the sense that they did not react with any of the above specified antigens. From the figure it is seen that 3 clones (F2, F10, F25) reacted exclusively with the peptide, 15 reacted with the peptide and $m\beta_2m$, and 3 (F5, F8, F26) reacted with the peptide, $m\beta_2m$ and $\beta_2m$ (native). The remaining 3 clones (F12, F18, F21) had lost reactivity.

Selection of hybridomas

All the hybridoma antibodies reacting with $m\beta_2m$ and/or $\beta_2m$ were further shown to be of the mouse immunoglobulin class Igm. This was found in experiments using the above mentioned ELISA procedure with a modification consisting of replacement of the peroxidaselabelled rabbit anti-mouse immunoglobulin with labelled antibodies specific for the murine classes and subclasses.

EXAMPLE 4

Mβ₂m as a biological response modifier

The activity of m-β₂m as a biological response modifier was assessed by the augmentation of one-way allogeneic mixed lymphocyte cultures (MLC).

Mixed lymphocyte reaction

Three different protocols were used.

1. The microculture method (Clasesson, M. H. and Miller, R. G. J. Immunol. 134 (1985) p. 684). Cultures were set up in replicates of four to six in 96-well conical microtitre trays (Nunc, Roskilde, Denmark). Responder cells, $2-5\times10^5$/culture, and mitomycin treated stimulator cells ($10^6$/culture), were cultured in a total volume of 200 μl.

2. Cultures were set up in $12\times75$ mm plastic tubes (Falcon, Oxnard, USA) using $0.5-1.0\times10^6$ mitomycin treated stimulator cells per ml in volumes of 1-2 ml.

3. Cultures were set up in 50 ml tissue culture flasks (Nunc) with $10^6$/ml responder and stimulator cells, respectively, in volumes of 5-10 ml. Native and modified β₂m were added to individual MLC at day 0 of culture, or in separate experiments at day 0 to 4 of culture.

Cytotoxicity assays

Cytotoxic activity of MLC cultures was determined after 5 days of culture in a 4 hour $^{51}$Cr-release assay. Target cells were $2-5\times10^3$ $^{51}$Cr-labelled RBL5 (H2$^b$), P815 (H-2$^d$) and YAC (NK target) tumor cell lines and in some experiments Concanavalin A induced spleen cell blasts from the MLC stimulator strain or an unrelated third party strain. Target cells, $1-5\times10^6$ cells in 0.1 ml fetal calf serum, were labelled with 150 μCi Sodium ($^{51}$Cr) chromate for 1-2 hours at 37° C. Cells were then washed four times before cytotoxicity assay. Spontaneous $^{51}$Cr release was determined from target cells added to cultures containing only mitomycin treated stimulator cells. Total releasable $^{51}$Cr was determined from acetic acid treated target cells. Per cent specific $^{51}$Cr release was calculated as: (observed release-spontaneous release)/(total release-spontaneous release)$\times100$.

In the microculture MLC, 0.1 ml supernatant was removed and replaced with 0.1 ml $^{51}$Cr-labelled target cells. In the culture tube and culture flask MLC systems, 0.1 ml volumes were added in replicates of four 96 well, V-bottom microtitre trays (Nunc) followed by addition of appropriate $^{51}$Cr labelled target cells in volumes of 0.1 ml. In separate experiments MLC responder cells were purified by centrifugation on Lymphopaque ® (Pharmacia, Sweden), and titrated against a constant number of target cells. After four hours of assay, culture volumes of 0.1 ml supernatant were removed for gamma counting.

Interleukin 2(IL-2) measurement

The IL-2 content was measured in duplicate two ml tube MLR cultures from day 1 to 4 of culture. Hundred μl of individual culture supernatants were added to three replicates of an IL-2 dependent CTL line, 4B3 (Curtis, A. S. G. and Rooney, P., Nature, London, 281 (1979) p. 222), kindly provided by Dr. R. G. Miller, the Ontario Cancer Institute, Toronto, Canada. The 4B3 CTL were cultured $5\times10^3$ cells per well, in flat bottom 96 well microtitre plates (Nunc) for 48 hours followed by addition of $^3$H-TdP (0.1 μCi per well) for 6 hours. Cells were harvested in a Scantron Cell Harvester (Oslo, Norway) and counted in a Scintillation counter.

Figure 8:
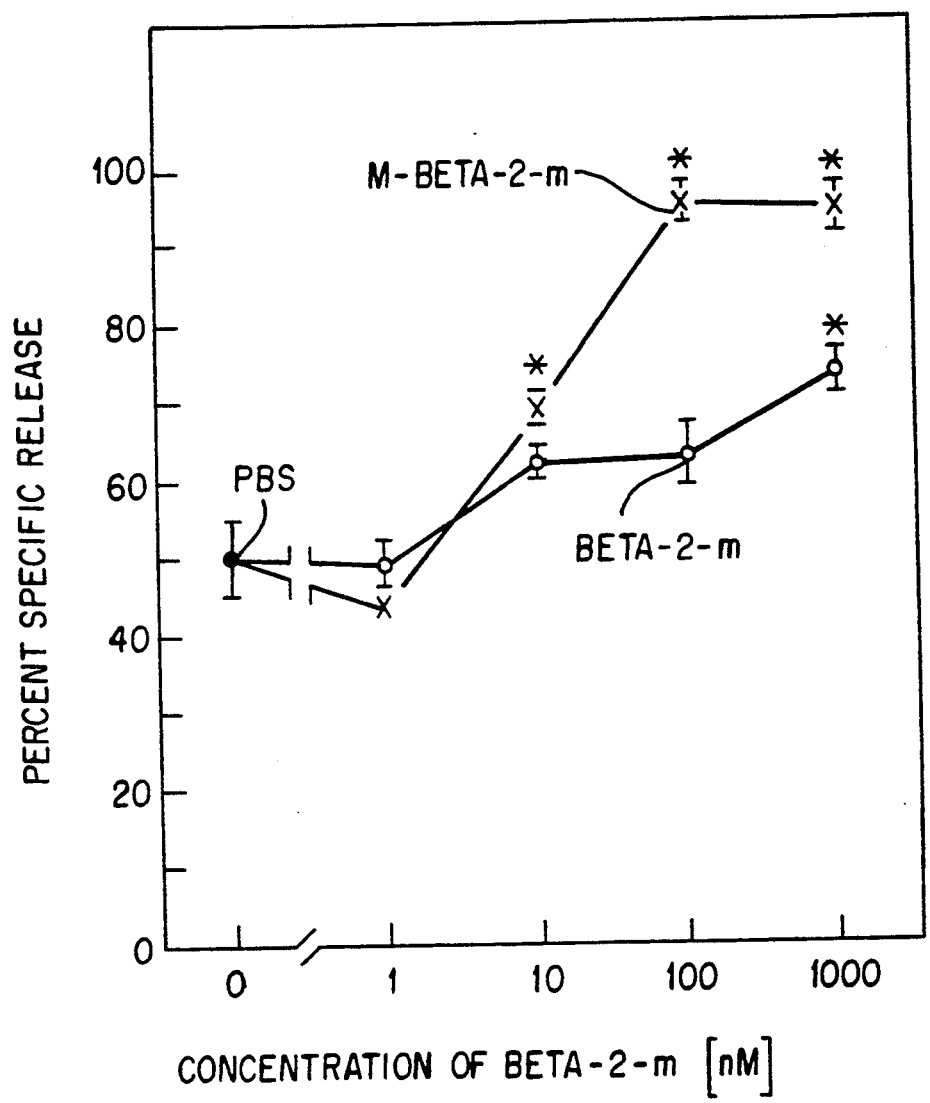
FIG. 8 shows the relation between cytotoxic activity of mixed lymphocyte cultures (MLC) and added m$\beta_2$m.

FIG. 8 shows that m-β₂m significantly (p<0.01) enhances the generation of cytotoxic lymphocytes (CTL) when added to the MLC at concentrations from 10-1000 nM. The functional activity of CTL generated in m-β₂m exposed MLC was specific since no cytotoxic activity was generated against third party haplotype or natural killer sensitive target cells. Furthermore, mβ₂m added directly to the cytotoxicity assay did not influence MLC generated killing by CTL.

The supernatants of MLC exposed to native or mβ₂m were examined for endogenous IL-2 production from day 1 to 4 of cultures. Data are shown in Table 7.

TABLE 7

IL-2 production in MLC exposed to β₂m and mβ₂m (200 nM/ml) and PBS. MLC consisted of $2\times10^6$ SJL anti $2\times10^6$ BALB/c in volumes of 2 ml. IL-2 production was tested on a IL-2 dependent CTL clone, 4B3.

| Addition | Units of IL2$^a$ per MLC culture | | | |
|---|---|---|---|---|
| | 1$^b$ | 2 | 3 | 4 |
| mβ₂m | 0 | 14 | 136 | 80 |
| β₂m | 2 | 12 | 42 | 104 |
| PBS | 0 | 16 | 28 | 70 |

$^a$One unit of IL-2 is defined as the amount of IL-2 which doubles the proliferative response of $5\times10^3$ 4B3 CTL in 48 hours cultures.
$^b$Days of MLC.

From Table 7 it is evident that mβ₂m stimulates the early (day 3) production of endogenous IL-2 as compared to native β₂m and PBS exposed MLC. However, in day-4 MLC cultures, the concentration of IL-2 was decreasing in mβ₂m exposed MLC, probably due to an increased rate of consumption by the proliferating CTLs at this time of culture. Mβ₂m by itself has no IL-2 like effect when tested directly on the cloned CTL line 4B3 (Curtis, A. S. G.. & Rooney, P., nature (London) 281 (1979 p. 281) used for the titration of IL-2 activity.

REFERENCES

1. Cunningham, B. A., Wang, J. L., Berggård, I. & Peterson, P. A. (1973) Biochemistry 12, 4811-4822.
2. Suggs, S. V., Wallace, R. B., Hirose, T., Kawashima, E. H. & Itakura, K. (1981) Proc. Natl. Acad. Sci. USA 78, 6613-6617.
3. Berggård I. Bearn A. G. (1968) J. Biol. Chem. 243, 4095-4103.
4. Plesner T. & Bjerrum O. J. (1980) Scand. J. Immunol. 11, 341-351.
5. Solheim, B. G. & Thorsby, E. (1974) Nature (Lond) 249, 36-38.
6. Peterson P. A., Rask, L. & Lindblom, J. B. (1974) Proc. Natl. Acad. Sci. USA 71, 35-39.
7. Cotner, J., Mashimo, H., Kung, P. G. Goldstein, G. & Strominger, J. L. (1981) Proc. Natl. Acad. Sci. USA 78, 3858-3862.
8. Terhorst, C., Agthoven, V. A., LeClair, K., Snow, P., Reinherz, E. & Schlossman, S. (1981) Cell 23, 771-780.
9. Peterson, P. A., Cunningham, B. A., Berggård, I. & Edelman, G. M. (1972) Proc. Natl. Acad. Sci. USA 69, 1697-1701.
18. Plesner, T., Wilken, M., Bjerrum, O. J. & Hansen, M. M. (1982) J. Clin. Lab. Immunol. 8, 137-141.
19. Weeke, B. (1973) in Manual of quantitative immunoelectrophoresis. Methods and applications. 1st edn. (Axelsen, N. H., Kroll, J. & Weeke, B., eds) pp. 47-56, Universitetsforlaget, Oslo.
20. Plesner, T., Nørgaard-Pedersen, B. & Boenisch T. (1975) Scand. J. Clin. Lab. Invest 35, 729-735.

22. Wycoff, M., Rodbard, A. & Chrambach, A. (1977) Anal. Biochem. 78, 459-482.
23. Bury, A. F. (1981) J. Chromathography 213, 491-500.
25. Moody, A. J., Thim, L. & Valverde, I. (1984) FEBS Lett. 172, 142-148.

What is claimed is:

1. A monoclonal antibody that specifically binds to modified $\beta_2$-microglobulin of formula I wherein formula I is:

$$R_1\text{---}Cys\text{---}R_2\text{---}X$$
$$|$$
$$Y\text{---}R_3\text{---}Cys\text{---}R_4$$

wherein $R_1$ is a 24-amino acid residue with the sequence Ile-Gln-Arg-Thr-Pro-Lys-Ile-Gln-Val-Tyr-Ser-Arg-His-Pro-Ala-Glu-Asn-Gly-Lys-Ser-Asn-Phe-Leu-Asn, $R_2$ is a 30-amino acid residue with the sequence Tyr-Val-Ser-Gly-Phe-His-Pro-Ser-Asp-Ile-Glu-Val-Asp-Leu-Leu-Lys-Asn-Gly-Glu-Arg-Ile-Gly-Lys-Val-Glu-His-Ser-Asp-Leu-Ser, $R_3$ is a 20-amino acid residue with the sequence Trp-Ser-Phe-Tyr-Leu-Leu-Tyr-Tyr-Thr-Glu-Phe-Thr-Pro-Thr-Glu-Lys-Asp-Glu-Tyr-Ala, $R_4$ is a 19-amino acid residue with the sequence Arg-Val-Asn-His-Val-Thr-Leu-Ser-Gln-Pro-Lys-Ile-Val-Lys-Trp-Asp-Arg-Asp-Met, X is Phe, Phe-Ser, or Phe-Ser-Lys, and Y is Asp, Lys-Asp, or Ser-Lys-Asp, wherein said monoclonal antibody specifically binds to modified $\beta_2$-microglobulin but does not bind to $\beta_2$-microglobulin.

2. A monoclonal antibody according to claim 1 wherein the immunogen used for immunizing an animal is an antigen selected from the group consisting of m$\beta_2$m, and compounds of the general formula II $$R\text{---}Z \qquad \qquad II$$

wherein R is a carrier protein, and Z is a peptide of the formula $R_2'$-X or $R_3'$-Y wherein X is Phe, Phe-Ser, or Phe-Ser-Lys, and Y is Asp, Lys-Asp, or Ser-Lys-Asp, $R_2'$ is a peptide with from 1 to 30 amino acid residues corresponding to a fragment from the C-terminal end of $R_2$ wherein $R_2$ is a 30-amino acid residue with the sequence Tyr-Val-Ser-Gly-Phe-His-Pro-Ser-Asp-Ile-Glu-Val-Asp-Leu-Leu-Lys-Asn-Gly-Glu-Arg-Ile-Gly-Lys-Val-Glu-His-Ser-Asp-Leu-Ser, and $R_3'$ is a peptide with from 1 to 20 amino acid residues corresponding to a fragment from the N-terminal end of $R_3$ wherein $R_3$ is a 20-amino acid residue with the sequence Trp-Ser-Phe-Tyr-Leu-Leu-Tyr-Tyr-Thr-Glu-Phe-Thr-Pro-Thr-Glu-Lys-Asp-Glu-Tyr-Ala.

3. The monoclonal antibody of claim 1 wherein said monoclonal antibody is a mouse monoclonal antibody.

4. The monoclonal antibody of claim 1 wherein said monoclonal antibody is detectably labeled.

5. The monoclonal antibody of claim 4 wherein said monoclonal antibody is radiolabeled.

6. The monoclonal antibody of claim 1 wherein said monoclonal antibody is bound to an insoluble solid phase.

7. A method for detecting modified $\beta_2$-microglobulin in human body fluid suspected of containing modified $\beta_2$-microglobulin, comprising contacting the body fluid with the monoclonal antibody of claim 1 detecting binding of said monoclonal antibody to m$\beta_2$m in said body fluid, and evaluating the presence of said m$\beta_2$m as a function of said binding of said monoclonal antibody to m$\beta_2$m.

8. The method of claim 7 wherein said method is selected from the group consisting of dot-blot analysis, immunometric sandwich assay, and competitive assay.

9. A method for detecting modified $\beta_2$-microglobulin in human body fluid suspected of containing modified $\beta_2$ microglobulin, comprising contacting the body fluid with the monoclonal antibody of claim 4 detecting binding of said monoclonal antibody to m$\beta_2$m in said body fluid, and evaluating the presence of said m$\beta_2$m as a function of said binding of said monoclonal antibody to m$\beta_2$m.

10. The method of claim 9 wherein said method is selected from the group consisting of dot-blot analysis, immunometric sandwich assay, and competitive assay.

11. A method for detecting modified $\beta_2$-microglobulin in human body fluid suspected of containing modified $\beta_2$ microglobulin, comprising contacting the body fluid with the monoclonal antibody of claim 6 detecting binding of said monoclonal antibody to m$\beta_2$m in said body fluid, and evaluating the presence of said m$\beta_2$m as a function of said binding of said monoclonal antibody to m$\beta_2$m.

12. The method of claim 11 wherein said method is selected from the group consisting of dot-blot analysis, immunometric sandwich assay, and competitive assay.

13. The monoclonal antibody of claim 1, wherein X is Phe and Y is Asp.

* * * * *

UNITED STATES PATENT AND TRADEMARK OFFICE
CERTIFICATE OF CORRECTION

PATENT NO.   : 5,175,113
DATED        : December 29, 1992
INVENTOR(S)  : Nissen, et al It is certified that error appears in the above-indentified patent and that said Letters Patent is hereby corrected as shown below:

In the right column of the cover sheet, the application number should read "500,919" and not "550,919."

Signed and Sealed this

Second Day of November, 1993

Attest:

BRUCE LEHMAN

Attesting Officer   Commissioner of Patents and Trademarks